(12) United States Patent
Tucker

(10) Patent No.: US 8,552,011 B2
(45) Date of Patent: Oct. 8, 2013

(54) 6-($C_{2-6}$ALKYLSELENO)PURINES AND METHODS FOR TREATING NEURAL MEASLES VIRAL INFECTION THEREWITH

(75) Inventor: William G. Tucker, Charlottetown (CA)

(73) Assignee: William G. Tucker, Charlottetown (CA)

( * ) Notice: Subject to any disclaimer, the term of this patent is extended or adjusted under 35 U.S.C. 154(b) by 219 days.

(21) Appl. No.: 12/995,004

(22) PCT Filed: Jun. 4, 2009

(86) PCT No.: PCT/CA2009/000770
§ 371 (c)(1),
(2), (4) Date: Nov. 29, 2010

(87) PCT Pub. No.: WO2009/146542
PCT Pub. Date: Dec. 10, 2009

(65) Prior Publication Data
US 2011/0086867 A1     Apr. 14, 2011

Related U.S. Application Data

(60) Provisional application No. 61/058,725, filed on Jun. 4, 2008.

(51) Int. Cl.
*A61K 31/522*     (2006.01)
*C07D 473/00*     (2006.01)

(52) U.S. Cl.
USPC ........................................ 514/263.3; 544/265

(58) Field of Classification Search
USPC ........................................ 544/265; 514/263.3
See application file for complete search history.

(56) References Cited

U.S. PATENT DOCUMENTS

2002/0058635 A1   5/2002   Averett

OTHER PUBLICATIONS

WebMD. Multiple Sclerosis Health Center. May 3, 2011. Available online at: http://www.webmd.com/multiple-sclerosis/guide/multiple-sclerosis-causes?print=true.*
International Search Report of PCT/CA2009/000770, Oct. 8, 2009.
Spratt, Thomas E., et al., "Reaction of O6—Alkylguanine-DNA Alkyltransferase with O6-Methylguanine Analogues: Evidence That the Oxygen of O6-Methylguanine Is Protonated by the Protein to Effect Methyl Transfer", Biochemistry 1992, 31, 3688-3694.
Maunter, Henry G., et al., "The Activity of 6-Selenopurine and Related Compounds against Some Experimental Mouse Tumors", Cancer Research, (1958), 18, pp. 294-298.
Maunter, Henry G., "The Synthesis and Properties of Some Selenopurines and Selenopyrimidines", Journal of the American Chemical Society, (1956), 78, pp. 5292-5294.
Shuie, C-Y, et al., "A New Alkylation Reagent for Seleno- and Thio-Substituted Nucleosides and Related Compounds", Journal of Organic Chemistry, (1976), 41(10), pp. 1847-1848.
European Search Report for EP 09757004.8, Feb. 21, 2012.
Tucker W.G., et al., "A Preliminary Evaluation of Azathioprine (Imuran) in the Treatment of Multiple Sclerosis", Henry Ford Hosp. Med. Journal, vol. 17, No. 2, 1969, pp. 89-92.
Chaudhuri, Abhijit et al., Multiple Sclerosis is Not an Autoimmune Disease, Arch. Neurol., vol. 61, pp. 1610-1612, Oct. 2004.
Ohara, Yoshiro, "Multiple Sclerosis and Measles Virus", Jpn. J. Infect. Dis, vol. 52, 1999, pp. 198-200.
Demir, Ercan, et al., "Atypical presentations of SSPA: A clinical study in four cases", The Turkish Journal of Pediatrics, 2007, vol. 49, pp. 295-300.
Burgoon, Mark P., et al. "Recombinant antibodies generated from both clonal and less abundant plasma cell immunoglobulin G sequences in subacute sclerosing panencephalitis brain are directed against measles virus", Journal of NeuroVirology, vol. 12, pp. 398-402, 2006.
Tucker, William G. et al., "A Preliminary Evaluation of Azathioprine (Imuran) in the Treatment of Multiple Sclerosis", Henry Ford Hosp. Med. Journal, vol. 17, No. 2, pp. 89-92, 1969.
Allen, Ingrid V., "The Significance of Measles Virus Antigen and Genome Distribution in the CNS in SSPE for Mechanisms of Viral Spread and Demyelination", Journal of Neuropathology and Experimental Neurology, vol. 55, No. 4, pp. 471-480, 1996.
Tucker, William G., et al., "The MSMV hypothesis: Measles virus and multiple sclerosis, etiology and treatment", Elsevier, Medical Hypothesis, pp. 1-8, 2008.
Transcript from Chemical Structure Search. Performed in STN's Chemical Abstracts Database on Oct. 25, 2007.
Transcript from Chemical Structure Search. Performed in STN's Chemical Abstracts Database on Nov. 29, 2007.
Transcript from Chemical Structure Search. Performed in STN's Chemical Abstracts Database on Nov. 28, 2007.

* cited by examiner

*Primary Examiner* — Noble Jarrell
*Assistant Examiner* — Laura Daniel
(74) *Attorney, Agent, or Firm* — Bereskin & Parr LLP/S.E.N.C.R.L., s.r.l.; Patricia Folkins

(57) ABSTRACT

The present application relates to anti-viral selenopurine compounds of formula (I): wherein $R^1$ is $C_{2-6}$alkyl, and pharmaceutically acceptable salts, solvates, and prodrugs thereof. These 6-($C_{2-6}$alkylseleno)purine compounds find use in the treatment of neural measles virus infection and associated diseases (namely, multiple sclerosis or neural measles). A particularly preferred compound is ethylselenopurine or ESP.

(I)

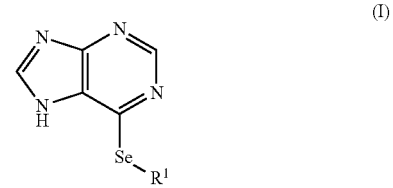

5 Claims, 2 Drawing Sheets

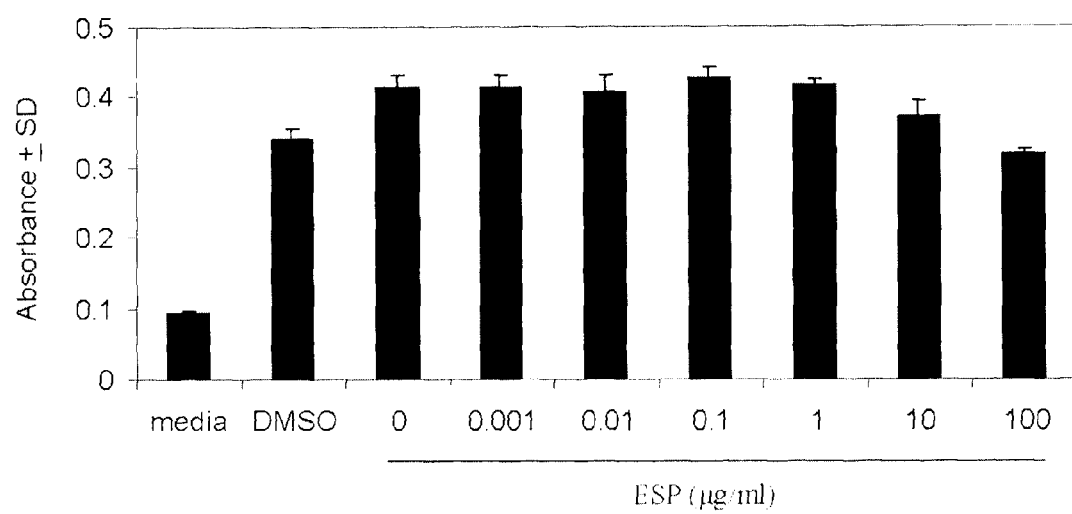
Fig 1. MTT assay data for HeLa cells treated for 24 h with ESP.

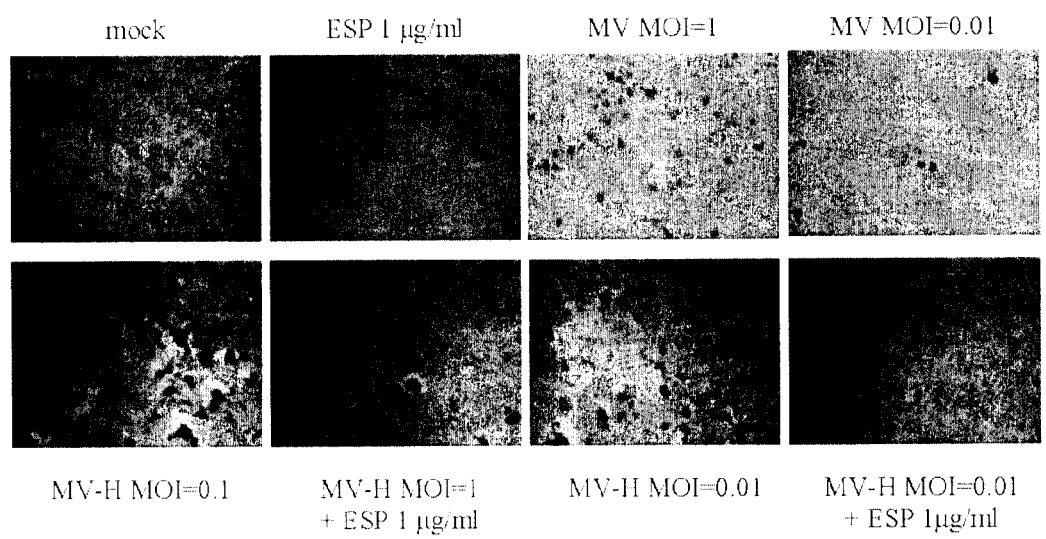
Fig 2. Representative images of HeLa cells infected with MV in the presence or absence of ESP

6-($C_{2-6}$ALKYLSELENO)PURINES AND METHODS FOR TREATING NEURAL MEASLES VIRAL INFECTION THEREWITH

This application is a National Stage of International Application No. PCT/CA2009/000770, filed Jun. 4, 2009, which claims the benefit of Provisional Application No. 61/058,725, filed Jun. 4, 2008, the contents of both of which are herein incorporated by reference in their entirety.

FIELD

The present application relates compounds and methods for treating neural measles viral infections or a disease associated therewith including, for example, neural measles and multiple sclerosis (MS). In particular the application relates to certain anti-viral seleno-purine compounds and their use to treat neural measles and MS.

BACKGROUND

Multiple sclerosis (MS) is a chronic inflammatory disease of the central nervous system (CNS). In pathology, the disease is characterized as scattered demyelination lesions, axonal loss and damage in both the brain and spinal cord (Lassmann, 2005), which results in a multiplicity of neurological deficits. Current therapies for managing patients with MS primarily target the inflammatory aspect of the disease (Zamvil and Steinman, 2003) and are only partly effective and limited by side effects. Recent studies suggest that glutamate-mediated cytotoxicity (excitotoxicity) (Stover et al., 1997; Barkhatova et al., 1998; Smith et al., 1999; Pitt, 2000), oxidative stress (Gilgum-Sherki et al., 2004) and mitochondrial damage (Andrews et al., 2005), may play vital roles in the pathogenesis of MS.

Measles is a member of the family Paramyxoviridae. Two types of measles virus are known, systemic measles and neural measles. While systemic measles causes the fever and rash generally associated with the measles virus. Neural measles virus is the etiology of sclerosing panencephalitis, which is an acute demyelinating disease (Sherman et al., 1965) with the pathologic characteristics of multiple sclerosis.

SUMMARY

The present application includes compounds selected from a compound of the formula I and pharmaceutically acceptable salts, solvates and prodrugs thereof:

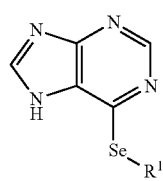

Formula I wherein $R^1$ is $C_{2-6}$alkyl.

The application also includes pharmaceutical compositions comprising a compound selected from a compound of formula I as defined above and a pharmaceutically acceptable salt, solvate or prodrug thereof and a pharmaceutically acceptable carrier.

The present application further includes a method of treating or preventing a neural measles viral infection or a disease associated therewith comprising administering to a subject in need thereof, an anti-viral effective amount of one or more compounds selected from a compound of Formula I, as defined above, and pharmaceutically acceptable salts, solvates and prodrugs thereof. In a further embodiment the disease is neural measles virus or MS.

The present application also includes a use of a compound selected from a compound of Formula I, as defined above, and pharmaceutically acceptable salts, solvates and prodrugs thereof, for the treatment or prevention of a neural measles viral infection or a disease associated therewith. In another embodiment the disease is neural measles or MS. Further, the present application includes a use of a compound selected from a compound of Formula I, and pharmaceutically acceptable salts, solvates and prodrugs thereof, to prepare a medicament for the treatment or prevention of a neural measles viral infection or a disease associated therewith. In a further embodiment the disease is neural measles or MS.

This Summary of Application lists several embodiments of the application, and in many cases lists variations and permutations of these embodiments. The Summary is merely exemplary of the numerous and varied embodiments. Mention of one or more specific features of a given embodiment is likewise exemplary. Such embodiment can typically exist with or without the feature(s) mentioned; likewise, those features can be applied to other embodiments of the application, whether listed in this Summary or not. To avoid excessive repetition, this Summary does not list or suggest all possible combinations of such features.

For purposes of summarizing the application and the advantages achieved over the prior art, certain objects and advantages of the application have been described above. Of course, it is to be understood that not necessarily all such objects or advantages may be achieved in accordance with any particular embodiment of the application. Thus, for example, those skilled in the art will recognize that the application may be embodied or carried out in a manner that achieves or optimizes one advantage or group of advantages as taught herein without necessarily achieving other objects or advantages as may be taught or suggested herein.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

BRIEF DESCRIPTION OF THE DRAWINGS

The application will now be described in relation to the drawings in which:

FIG. 1 shows MTT assay data for HeLa cells treated for 24 h with ESP and

FIG. 2 shows representative images of HeLa cells infected with MV in the presence or absence of ESP.

DETAILED DESCRIPTION OF THE APPLICATION

It has been found that in a sample of patients with confirmed diagnosis of multiple sclerosis, the patients were found to have increased gamma globulin, and elevated measles titer in the cerebral spinal fluid but had normal to absent measles titer in the serum. It is known that neural measles causes sclerosing panencephalitis, which is an acute demyelinating disease. It is postulated that MS is a slow relapsing form of neural measles virus and could therefore be treated by treating the neural measles virus. Further it has been found that the seleno-purine compounds of the application act as anti-viral compounds against neural measles virus and are therefore useful in therapy in particular in the treatment of neural measles and MS.

(I) DEFINITIONS

The term "$C_{2-6}$alkyl" as used herein means straight and/or branched chain, saturated alkyl radicals containing from 2 to 6 carbon atoms and includes ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like.

The term "tautomer" as used herein refers to compounds that are interconvertible by a formal migration of a hydrogen atom or proton, accompanied by a switch of a single bond and an adjacent double bond. In solutions where tautomerization is possible, a chemical equilibrium of the tautomers will be reached. The exact ratio of the tautomers depends on several factors, including temperature, solvent and pH.

The term "compounds of the application" as used herein refers to a compound selected from a compound of Formula I, and pharmaceutically acceptable salts, solvates and prodrugs thereof.

It is to be clear that the present application includes pharmaceutically acceptable salts, solvates and prodrugs of compounds of the application and mixtures comprising two or more of compounds of Formula I, pharmaceutically acceptable salts of the compounds of Formula I, pharmaceutically acceptable solvates of compounds of Formula I and prodrugs of compounds of Formula I.

The term "pharmaceutically acceptable" means compatible with the treatment of animals, in particular, humans.

The term "pharmaceutically acceptable salt" as used herein means an acid addition salt which is suitable for or compatible with the treatment of patients.

The term "pharmaceutically acceptable acid addition salt" as used herein means any non-toxic organic or inorganic salt of any base compound of the application, or any of its intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the formula I, for laboratory use, or for subsequent conversion to a pharmaceutically acceptable acid addition salt. In embodiments of the application, the pharmaceutically acceptable acid addition salt is the hydrochloride salt.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound of the formula I or a pharmaceutically acceptable salt of a compound of the formula I, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions.

Compounds of the formula I include prodrugs. In general, such prodrugs will be functional derivatives of a compound of the formula I which are readily convertible in vivo into the compound from which it is notionally derived. Prodrugs of the compounds of the formula I may be conventional esters or amides formed with an available amino group. For example, an available nitrogen in a compound of the formula I may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In certain instances, the prodrugs of the compounds of the formula I are those in which one or more of the hydroxy groups in the compounds is masked as a group which can be converted to a hydroxy group in vivo. Conventional procedures for the selection and preparation of suitable prodrugs are described, for example, in "Design of Prodrugs" ed. H. Bundgaard, Elsevier, 1985.

Compounds of the formula I include radiolabeled forms, for example, compounds of the formula I labeled by incorporation within the structure $^{3}H$ or $^{14}C$ or a radioactive halogen such as $^{125}I$. A radiolabeled compound of the formula I may be prepared using standard methods known in the art. For example, tritium may be incorporated into a compound of the formula I using standard techniques, for example by hydrogenation of a suitable precursor to a compound of the formula I using tritium gas and a catalyst. Alternatively, a compound of the formula I containing radioactive iodo may be prepared from the corresponding trialkyltin (suitably trimethyltin) derivative using standard iodination conditions, such as [$^{125}I$] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C.

(II) COMPOUNDS OF THE APPLICATION

The present application includes compounds selected from a compound of the formula I and pharmaceutically acceptable salts, solvates and prodrugs thereof:

Formula I wherein $R^1$ is $C_{2-6}$alkyl.

In a particular embodiment $R^1$ is ethyl.

(III) METHODS OF PREPARING COMPOUND OF THE APPLICATION

In accordance with another aspect of the present application, the compounds of Formula can be prepared using the methods described herein. Accordingly, the present application also includes a method of preparing a compound of Formula I comprising reacting a 6-chloropurine (1) with selenourea (2) to give intermediate selenopurine (3) which may then be reacted with an alkyl iodide to provide a compound of formula I, wherein $R^1$ is $C_{2-6}$alkyl.

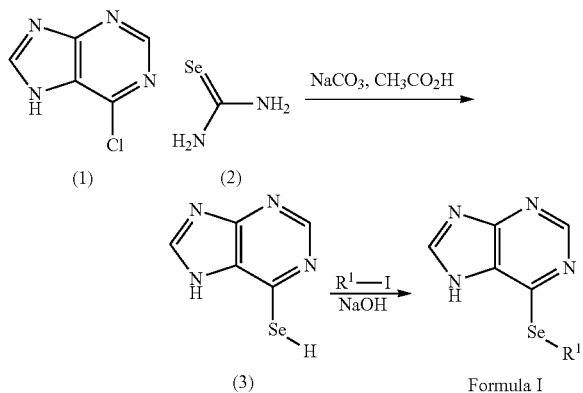

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, $3^{rd}$ Edition, 1999.

As hereinbefore mentioned, novel compounds of the Formula I have been prepared. Accordingly, the present application includes all uses of the compounds of the application including their use in therapeutic methods and compositions as anti-virals and in the treatment or prevention of neural measles and MS, their use in diagnostic assays and their use as research tools. In particular, the present application includes the use of a compound of the application as a medicament, and further includes the use of a compound of the application as a medicament for the treatment or prevention of neural measles and MS.

(IV) COMPOSITIONS AND THERAPEUTIC METHODS AND USES

The present application includes pharmaceutical composition comprising a compounds of formula I or pharmaceutically acceptable salt, solvate or prodrug thereof and a pharmaceutically acceptable carrier.

The present application includes a method of treating or preventing a neural measles viral infection or a disease associated therewith comprising administering an effective amount of a compound of the application to a subject in need thereof. In a further embodiment of the application the disease is neural measles or MS.

The present application also relates to a use of a compound of the application for the treatment or prevention of a neural measles viral infection or a disease associated therewith. In a further embodiment the disease is neural measles or MS. Further, the present application relates to the use of a compound of the application to prepare a medicament for the treatment or prevention of a neural measles viral infection or a disease associated therewith. In a further embodiment the disease is neural measles or MS.

The term "subject" as used herein includes all members of the animal kingdom including human. The subject is suitably a human.

The term a "therapeutically effective amount", "effective amount" or a "sufficient amount" of a compound of the present application is a quantity sufficient to, when administered to the subject, including a mammal, for example a human, effect beneficial or desired results, including clinical results, and, as such, an "effective amount" or synonym thereto depends upon the context in which it is being applied. For example, in the context of treating or preventing neural measles viral infection, for example, it is an amount of the compound sufficient to achieve such treatment or prevention of neural measles viral infection as compared to the response obtained without administration of the compound. In the context of disease, therapeutically effective amounts of the compounds of the present application are used to treat, modulate, attenuate, reverse, or effect diseases associated with neural measles viral infections in a mammal. Therefore an "effective amount" is intended to mean that amount of a compound that is sufficient to treat, prevent or inhibit neural measles viral infection or a disease associated with neural measles viral infection. The amount of a given compound of the present application that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound of the present application is an amount which prevents, inhibits, suppresses or reduces neural measles viral infection (e.g., as determined by clinical symptoms or the amount of virus) in a subject as compared to a control. As defined herein, a therapeutically effective amount of a compound of the present application may be readily determined by one of ordinary skill by routine methods known in the art.

To "inhibit" or "suppress" or "reduce" a function or activity, such as neural measles viral infection, is to reduce the function or activity when compared to otherwise same conditions except for a condition or parameter of interest, or alternatively, as compared to another condition.

As used herein, and as well understood in the art, "treating" or "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder, means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with an neural measles viral infection or manifesting a symptom associated with a disease associated therewith.

The compounds of the application may be used in the form of the free base, in the form of salts, solvates and/or prodrugs. All forms are within the scope of the application. Suitably the compound is used in the form of a free base or a pharmaceutically acceptable salt.

In accordance with the methods and uses of the application, the compound of the application, and/or salts, solvates and/or prodrugs thereof, may be administered to a patient in a variety of forms depending on the selected route of administration, as will be understood by those skilled in the art. A compound of the application, and/or salts, solvates and/or prodrugs thereof, may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the application, and/or salts, solvates and/or prodrugs thereof, may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound may be incorporated with excipient and used in the form of ingestible tablets, buccal tablets, troches, capsules, elixirs, suspensions, syrups, wafers, and the like.

A compound of the application, and/or salts, solvates and/or prodrugs thereof, may also be administered parenterally. Solutions of a compound of the application can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2000-20th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases, the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

A compound of the application, and/or salts, solvates and/or prodrugs thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

A compound of the application, and/or salts, solvates and/or prodrugs thereof, may also be delivered by the use of monoclonal antibodies as individual carriers to which the compound molecules are coupled. A compound of the application, and/or salts, solvates and/or prodrugs thereof, may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, a compound of the application, and/or salts, solvates and/or prodrugs thereof, may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and crosslinked or amphipathic block copolymers of hydrogels.

Compounds of the application, and/or salts, solvates and/or prodrugs thereof, may be used alone or in combination with other known agents useful for treating or preventing viral infections such as neural measles viral infection or a disease associated therewith.

When used in combination with other agents useful in treating demyelination diseases, compounds of the application, and/or salts, solvates and/or prodrugs thereof, is suitably administered contemporaneously with those agents. As used herein, "contemporaneous administration" of two substances to an individual means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances.

Compounds of the application, and/or salts, solvates and/or prodrugs thereof, may be administered to an animal alone or also in combination with pharmaceutically acceptable carriers, as noted above, the proportion of which is determined by the solubility and chemical nature of the compound, chosen route of administration and standard pharmaceutical practice.

The dosage of compounds of the application, and/or salts, solvates and/or prodrugs thereof, can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. Compounds of the application, and/or salts, solvates and/or prodrugs thereof, may be administered initially in a suitable dosage that may be adjusted as required, depending on the clinical response. As a representative example, oral dosages of compounds of the application, and/or salts, solvates and/or prodrugs thereof, will range between about 1 mg per day to about 400 mg per day for an adult, suitably about 1 mg per day to about 200 mg per day, more suitably about 1 mg per day to about 20 mg per day. When formulated for oral administration, the compounds are suitably in the form of tablets containing 0.25, 0.5, 0.75, 1.0, 5.0, 10.0, 20.0, 25.0, 30.0, 40.0, 50.0, 60.0, 70.0 75.0, 80.0, 90.0, 100.0 150, 200, 250, 300, 350 or 400 mg of active ingredient per tablet. Suitably, for oral administration, the compounds are suitably in the form of tablets containing 0.25, 0.5, 0.75, 1.0, 5.0 or 10.0, mg of active ingredient per tablet. Compounds of the application, and/or salts, solvates and/or prodrugs thereof, may be administered in a single daily dose or the total daily dose may be divided into two, three of four daily doses. If the compound of the application, and/or salts, solvates and/or prodrugs thereof, are to be administered transdermally, using, for example, those forms of transdermal skin patches that are well known to those skilled in the art, the dosage administration will be continuous rather than intermittent throughout the dosage range.

In an embodiment of the application, the compound of the application, and/or salts, solvates and/or prodrugs thereof, is administered or used long term or chronically. The term "long term" or "chronic" and use or administration as used herein means that the compound of the application, and/or a pharmaceutically acceptable salt, solvate and prodrug thereof, is administered to a subject on a continuous regular, long-term therapeutic basis. For example, the compound of the application, and/or a pharmaceutically acceptable salt, solvate and prodrug thereof, may be administered to a subject without substantial interruption, such as, for example, daily, for a time period of at least several weeks or months to several years, for the purpose of treating the demyelination disease in a subject needing treatment. In an embodiment of the application, the compound of the application, and/or a pharmaceutically acceptable salt, solvate and prodrug thereof, is administered to a subject for at least about 2 months. In a further embodiment of the application, the compound of the application, and/or a pharmaceutically acceptable salt, solvate and prodrug thereof, is administered to a subject on an indefinite basis, for example for the rest of the subject's life, or until such administration does not have a beneficial effect or treatment.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

EXAMPLES

Example 1

Synthesis of Compounds

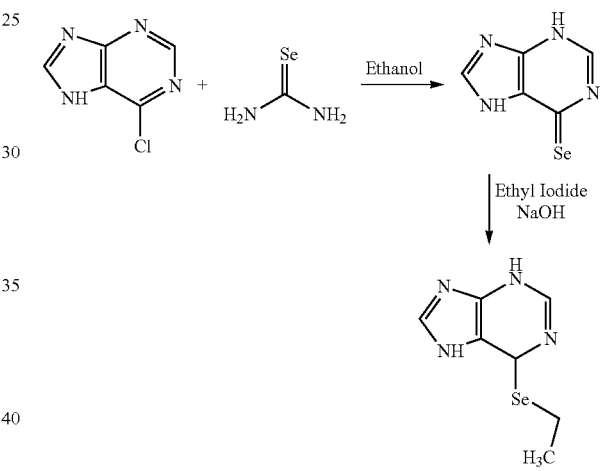

(a) A 250 ml round bottom flask (RBF) was charged with 30 ml of dry ethanol. To the dry ethanol was added 2 grams (0.0129 moles) of 6-chloropurine and 1.62 grams of selenourea. The reaction was brought to reflux. Reaction was stirred at reflux for 1 hour, then left to stir at R.T. overnight. A muddy orange precipitate was filtered. The muddy orange precipitate was transferred back into a 250 ml RBF. A 2% solution of sodium bicarbonate (200 ml) was prepared and heated to 50 C together with the muddy orange precipitate. This was stirred for 5 to 10 minutes and a fine dark precipitate emerged. This was filtered through a 1 micron glass fiber filter. The mother liquors were cooled to room temperature and 9 ml of acetic acid was carefully added. Some foaming occurred but was controllable. An orange solid was filtered, then dried at 65° C. for 2 hours in vacuum.
Total 1.80 grams (65% yield)
(b) A 100 ml RBF was charged with 1.70 grams (7.85 mmoles) of selenopurine and 18.25 ml of a 0.43 Molar sodium hydroxide solution. To this solution was added 0.63 ml of ethyl iodide. The solution was stirred for 2 hours. The clear solution turned over the course of the two hours to have a fine yellow precipitate. The pH was still in the 9 to 10 range. An additional 0.03 ml of ethyl iodide was added and stirring continued for 1 more hour. The pH was then adjusted to 2 with acetic acid and an orange solid product was filtered. Upon drying the solid weighed 1.0 grams.

Total 1.0 grams (51%)

Example 2

Anti-Viral Activity

A compound of the application was tested for cytotoxicity and for anti-viral effect on measles virus (MV) and human herpes simplex virus (HSV).

Materials and Methods

Compound preparation: Stock solutions of the test compound (termed ethylselenopurine or ESP) were prepared in dimethylsulfoxide at 10 mg/ml followed by sonication for 20 min at room temperature (RT) to ensure complete solubilization. Working concentrations were subsequently prepared in DMSO from the stock solution at concentrations that ensured a final vehicle concentration of 0.1% (v/v) and stored in 50 μl aliquots at −20° C. until used.

Cells and cell culture: HeLa cells (human cervical carcinoma) were used for these studies. Cells were maintained in DMEM medium supplemented with 10% fetal calf serum (FCS) and antibiotics in a humidified, 5% $CO_2$ environment. Cells were passaged as required by trypsinization.

Viruses: Two strains of measles virus (MV) were evaluated in this study: 1) strain Edmonston (MV-E), the prototypical lab-adapted strain originally derived from the blood of a human patient in the acute phase of a typical infection, and 2) strain Halle (MV-H), a neurovirulent strain derived from a lymph node biopsy of a human patient with subacute sclerosing panencephalitis. One strain of herpes simplex virus (HSV) was evaluated: HSV-2 (strain G). This strain is a primary isolate derived from an active genital infection.

Evaluation of toxicity: Acute toxicity was quantified using a standard tetrazole reduction assay as a measure of cell proliferation/viability. Briefly, quadruplicate wells of HeLa cells ($1 \times 10^4$ cells, 96-well plates) were incubated for 24 h with the ESP or DMSO as a control and the reduction of tetrazolium salt (MTT) to purple formazan by mitochondrial reductases enzymes in viable cells detected as a change in absorbance ($\lambda$=500-600 nm). Overt cytotoxicity was also evaluated qualitatively by microscopic analysis over longer exposure periods during the antiviral tests. Toxicity was considered to be evident if cell injury or loss was observed or a reduction in MTT activity of greater than twenty-five percent relative to controls was detected.

Infection conditions: Cells ($4 \times 10^4$ cells/well) were seeded in 24-well culture plates and pre-treated with ESP for 24 hr prior to infection. Cells were incubated with 100 μl of MV at the indicated MOI for 1 h at 37° C. before conditioned media containing the test compound and 5% FCS was replaced for the assay duration. MV replication was evaluated daily by microscopic analysis until cells were stained with 0.1% cresyl violet dye and scored for cytopathic effects. Similar conditions were employed for HSV-2 with the exception that infections were performed at 35° C. over a test period of 72 h.

Results

Four independent experiments were performed over the course of the evaluation. These are summarized as follows:

(1)—Evaluation of acute toxicity: ESP was assessed by MTT assay as described above using a series of dilutions (w/v): 65, 10, 1, 0.1, 0.01, 0.001 and 0 ng/ml. For all test concentrations, DMSO content was equalized to 0.1% (v/v) to minimize vehicle-associated effects. Toxicity was evaluated over a 24 h incubation period, a time period that corresponded to the pre-treatment phase of the anti-viral testing protocol. As shown in FIG. 1, toxicity was not observed with HeLa cells at any of the test concentrations.

(2)—Preliminary anti-viral screening: ESP was initially evaluated for antiviral activity using MV-E and MV-H. For these studies, three MOIs of the viruses (1.0, 0.1, 0.01) and six concentrations of ESP (65, 10, 1, 0.1, 0.01, 0 μg/ml) were investigated. Consistent with Experiment 1, no toxicity was evident with ESP during the 24 h pre-treatment phase before infection. However, overt cytotoxicity was observed at 24 h post-infection (PI) with 65 μg/ml of ESP and at 72 h PI with 10 μg/ml. No toxicity was observed with concentrations less than or equal to 1 μg/ml even at time-frames approaching one week. Syncytia formation in MV-E infected wells was first observed at 72 h PI and the infection had progressed sufficiently for antiviral activity to be evaluated by Day 5 PI. However, syncytia formation did not differ between treated and untreated wells. In comparison, syncytia were first observed in wells infected with the slower replicating, neurovirulent MV-H strain at Day 4 PI. By Day 5 PI, a decrease in syncytia formulation was evident in MV-H infected cells treated with ESP compared to vehicle controls.

(3)—Anti-MV screening: ESP was re-evaluated using MV-E and MV-H under a protocol modified in an attempt to avoid the effects of toxicity. Again, the viruses were investigated at three MOIs (1.0, 0.1, 0.01) using ESP used at 5, 2.5, 1, 0.5, 0.25, 0.1 and 0 ng/ml. The toxicity of ESP for HeLa cells at concentrations exceeding 1 μg/ml was confirmed when toxic effects were observed at 5 and 2.5 μg/ml by 72 h PI. As with the first trial, ESP did not significantly decrease syncytia formation in cells infected with MV-E compared to untreated controls. In contrast, syncytia formation in MV-H infected cells was reduced in a dose-dependent manner following ESP treatment, ranging from 66% with 1 μg/ml ESP to 25% with 0.1 μg/ml ESP (FIG. 2).

(4)—Anti-HSV screening: ESP was evaluated at 1, 0.5. 0.25, 0.1 and 0 μg/ml against HSV-2 at MOI=I, 0.1 and 0.01. No difference in viral replication, as evidenced by plaque formation, was observed in ESP-treated cells relative to vehicle controls.

CONCLUSIONS AND ANALYSIS

ESP exhibits cytotoxic/anti-proliferative activity against human HeLa cells in a dose- and time-dependent fashion. For HeLa cells, concentrations not exceeding 1 μg/ml may be used in the absence of toxic effects. A concentration of 1 μg/ml corresponds to a dose of 0.1 μg of ESP being delivered to the cells in culture.

ESP exhibits anti-viral activity against the Halle strain of MV that is both viral titer and concentration dependent. It should be noted that MV-H is a slower replicating isolate derived from a patient with subacute sclerosing panencephalitis, a condition that closely mimics the pathology of progressive neurological diseases in which myelin degeneration and loss is a primary symptom, including Multiple Sclerosis. Both MV-E and HSV-2, which replicate comparatively faster than MV-H, were unaffected by ESP. MV and HSV-2 belong to distinct virus families with greatly different infection requirements and host cell dependencies. Thus, it is unlikely that any one drug would influence both MV and HSV-2 without being toxic to the host cell. The differences observed between MV-E and MV-H are more intriguing and suggests the potential for ESP to inhibit neurovirulent measles strains.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS
REFERRED TO IN THE SPECIFICATION

Andrews H E, Nichols P P, Bates D, Turnbull D M. 2005. Mitochondrial dysfunction plays a key role in progressive axonal loss in multiple sclerosis. Med Hypotheses 64 (4): 669-677.
Barkhatova V P, Zavalishin I A, Askarova L Sh, Shavratskii V Kh, Demina E G. 1998. Changes in neurotransmitters in multiple sclerosis. Neurosci Behav Physiol 28 (4):341-344.
Gilgun-Sherki Y, Melamed E, Offen D. 2004. The role of oxidative stress in the pathogenesis of multiple sclerosis: the need for effective antioxidant therapy. J Neurol. 251 (3):261-268.
Lassmann H. 2005. Multiple sclerosis pathology: evolution of pathogenetic concepts. Brain Pathol. 2005 July; 15(3): 217-222.
Pitt D, Werner P, Raine C S. 2000. Glutamate excitotoxicity in a model of multiple sclerosis. Nat. Med. (1):67-70.
Sherman F E, Michaels R H, Kenny F M. Acute Encephalopathy Complicating Rubella. JAMA. 1965; 192:675
Smith K J, Kapoor R, Felts P A. 1999. Demyelination: the role of reactive oxygen and nitrogen species. Brain Pathol. 9 (1), 69-92.
Stover J F, Pleines U E, Morganti-Kossmann M C, Kossmann T, Lowitzsch K, Kempski O S. 1997. Neurotransmitters in cerebrospinal fluid reflect pathological activity. Eur J Clin Invest 27 (12):1038-1043.
Zamvil, S S and Steinman L. 2003. Diverse targets for intervention during inflammatory and neurodegenerative phases of multiple sclerosis. Neuron 38(5):685-688.

What is claimed is:

1. A compound of Formula 1 or pharmaceutically acceptable salts thereof:

Formula 1 wherein $R^1$ is $C_{2-6}$alkyl.

2. The compound according to claim 1, wherein $R^1$ is ethyl.

3. A composition comprising a compound according to claim 1 and a pharmaceutically acceptable carrier.

4. A method of treating a neural measles viral infection, comprising administering to a patient in need thereof an effective amount of a compound of Formula 1

Formula 1 of a pharmaceutically acceptable salt thereof.

5. The method according to claim 4, wherein the neural measles virus infection leads to neural measles in the subject and the neural measles is treated.

* * * * *